(12) United States Patent
Barta et al.

(10) Patent No.: US 6,979,123 B2
(45) Date of Patent: Dec. 27, 2005

(54) METHOD AND APPARATUS FOR BALANCING A STATICALLY UNBALANCED ARM IN AN X-RAY SYSTEM

(75) Inventors: Tamas Barta, Budaors (HU); Zoltan Baranyai, Tatabanya (HU)

(73) Assignee: General Electric Company Medical Systems Group, Milwaukee, WI (US)

( * ) Notice: Subject to any disclaimer, the term of this patent is extended or adjusted under 35 U.S.C. 154(b) by 215 days.

(21) Appl. No.: 10/418,758

(22) Filed: Apr. 18, 2003

(65) Prior Publication Data

US 2004/0208289 A1    Oct. 21, 2004

(51) Int. Cl.[7] ................................................ A61B 6/04
(52) U.S. Cl. ....................................... 378/197; 378/37
(58) Field of Search .............................. 378/196–197, 378/37, 201, 167

(56) References Cited

U.S. PATENT DOCUMENTS

| | | |
|---|---|---|
| 4,969,174 A | 11/1990 | Scheid et al. |
| 4,998,270 A | 3/1991 | Scheid et al. |
| 5,007,428 A | 4/1991 | Watmough |
| 5,018,176 A | 5/1991 | Romeas et al. |
| 5,305,365 A | 4/1994 | Coe |
| 5,388,141 A * | 2/1995 | Hove ......................... 378/197 |
| 5,506,877 A | 4/1996 | Niklason et al. |
| 5,539,797 A | 7/1996 | Heidsieck et al. |
| 6,142,667 A | 11/2000 | Pattee |

* cited by examiner

*Primary Examiner*—Edward J. Glick
*Assistant Examiner*—Hoon Song
(74) *Attorney, Agent, or Firm*—Quarles & Brady LLP

(57) ABSTRACT

A method and apparatus for balancing a statically unbalanced system, particularly useful in balancing X-ray and mammography systems having an X-ray source and detector mounted to a rotational arm, includes a linear actuator coupled to a drive mechanism which synchronizes the activation of the linear actuator with the rotation of the arm of the mammography system. The drive mechanism can include intermeshed gears, wheels or gears coupled together with a chain or belt, or other types of synchronizing drives. The balancing mechanism reduces the amount of force necessary to rotate the arm and decreases the overall weight of the system by eliminating the need for counterweights to maintain balance of the system.

17 Claims, 6 Drawing Sheets

METHOD AND APPARATUS FOR BALANCING A STATICALLY UNBALANCED ARM IN AN X-RAY SYSTEM

CROSS-REFERENCE TO RELATED APPLICATION

Not applicable.

STATEMENT REGARDING FEDERALLY SPONSORED RESEARCH OR DEVELOPMENT

Not applicable.

BACKGROUND OF THE INVENTION

In a number of clinical applications, X-ray apparatuses which include an X-ray source and X-ray detector mounted to a rotational arm are common. These systems provide the ability to rotate the X-ray source and detector to varying angles to obtain images without requiring the patient to move. A mammography system, for example, typically comprises an X-ray source, an X-ray detector, a breast support plate, and a breast compression plate. The source and detector are mounted to opposing ends of an arm, such as a C-arm, and the arm is disposed to rotate around the breast support and compression plates. The breast is positioned between the breast support and breast compression plates to hold the breast in place during mammography, and is arranged between the source and the receiver on the opposing ends of the C-arm. During mammography, the C-arm is rotated about the breast plates such that images of the breasts are acquired from varying angles.

For construction reasons, and due to the varying weights of the components, the center of mass of the rotatable C-arm is typically spaced apart from the axis of rotation, and is therefore "unbalanced" about the axis of lateral rotation. In an unbalanced system, a significant torsional force must be applied to rotate the arm to a desired position. It is desirable, however, to reduce the amount of force required to rotate the arm, to simplify use of the equipment for medical personnel.

To balance the system, counterweights are typically used to provide a counteractive torsional force. While counterweights significantly reduce the torsional force that must be applied when rotating the arm, they add significantly to both the weight and cost of the system. Furthermore, the counterweights make it very difficult to move the mammography system from place to place when desired. It is desirable, therefore, to provide alternate methods for balancing a mammography or other imaging system comprising an arm in which the torsional force required for rotation is reduced.

SUMMARY OF THE INVENTION

In one aspect, the invention comprises an X-ray apparatus including an arm rotatably coupled to a pivot point on a base support, the arm including an X-ray source and an X-ray detector coupled to opposing ends. A linear actuator is pivotally coupled to the base support at one end and to a drive mechanism at the opposing end. The drive mechanism synchronizes the axis of rotation of the arm with the axis of rotation of the linear actuator such that a force applied by the linear actuator at a contact point on the drive mechanism balances a torque force of the arm.

In another aspect, the invention comprise an X-ray apparatus including a base support, a rotational member pivotably coupled to the base support, and an arm having an X-ray source coupled to the first end and an X-ray detector coupled to the second end. The arm is mounted to the rotational member for rotation relative to the base support. A first cogwheel is coupled to the rotational member, and a second cogwheel is meshed with the first cogwheel. A constant force linear actuator is coupled between the second cogwheel and to the base support, an active connection provided at the cogwheel and an inactive connection at the base support. As the arm is rotated the first and second cogwheels maintain a one to one correspondence between an angle of rotation of the arm and an angle of rotation of the active connection point of the linear actuator, such that the constant force linear actuator applies a torsional force to counterbalance the torque force of the arm and to provide a substantially statistically balanced system.

Another aspect of the invention is to provide a statically balanced mammography system. The mammography system comprises a base support, an arm rotatably coupled to the base support, and a linear actuator rotatably coupled to the base support at a first end and to a rotational member at a second end. The linear actuator applies an upward force at a connection point between the linear actuator and the rotational member. A drive mechanism is coupled between the rotational member and the arm, wherein as the arm is rotated, the drive mechanism synchronizes the angle of rotation of the arm with the angle of rotation of the connection point such that the applied force of the linear actuator counteracts the torque force of the arm to balance the torsional force of the arm.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE INVENTION

Figure 1:
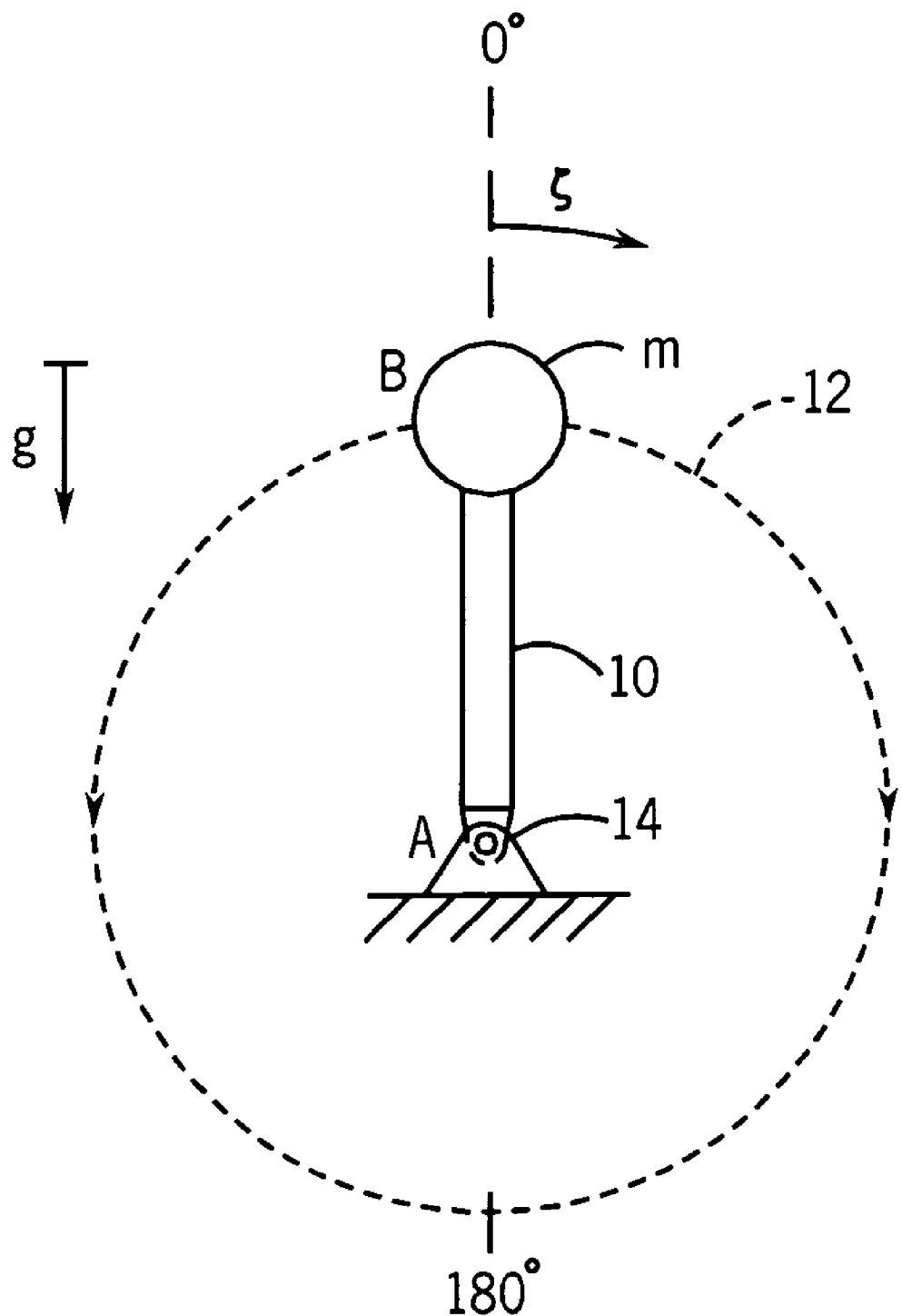
FIG. 1 is an illustration of a mass rotatably mounted to a rotatable arm.

Referring now to FIG. 1, an arm 10 having a length AB and comprising a rotating body 12 having mass "m", and a center of mass "B" is rotatable about an axis of rotation 14 or pivot point "A". When the arm 10 is released from a static position, the arm rotates around the rotation of axis 14 in a direction determined by the force of gravity "g" the arm reaches a stable position when the direction of the arm 10 correlates with the direction of the gravity vector "g", and therefore when the angle of rotation is either zero or one hundred and eighty degrees. When released from a stable position, as shown, at which the angle of rotation is $\phi=0°$, the direction of motion of the arm around the axis 14 is downward, and, as required by the principle of minimum potential, stabilizes at the angle $\phi=180°$. As the arm rotates, the torque force of the arm ($M_A$ ($\phi$) at a given rotational angle is defined by the following equation:

$$M_A(\phi) = m*g*AB*\sin \phi.\qquad [\text{equation 1}]$$

As described above, the minimum potential stable position for the mass "B" is $\phi=180$, with the center of mass directly below the axis of rotation 14. To balance the system to maintain the unbalanced body in a static position which is not equivalent to 180 degrees, an opposing torque must be applied to counter the torque "$M_A$ ($\phi$)" of the center of mass "B".

Figure 2:
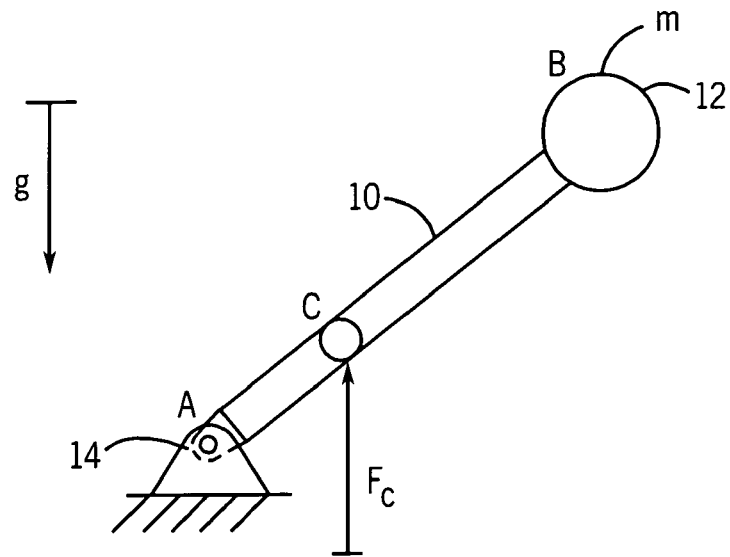
FIG. 2 is an illustration of a counteractive force for balancing the system of FIG. 1.

Referring now to FIG. 2, to provide a counteractive torque, a mechanism which is rotatable about the minimum potential static resting point (i.e. the one hundred and eighty degree resting point) of the center of mass B and which provides an active force on the arm 10 in a circular path can be provided to deliver a torque in the direction opposite to and of substantially the same magnitude as the torque "$M_A$ ($\phi$)". Here, the counteractive force is $F_C$, and is directed at an active contact point 21(C) on the arm 10, located a distance AC along the arm 10. Referring again to equation 1, to balance the torque "$M_A$ ($\phi$)", the counteractive torque must be equivalent to the downward torque of the arm. Therefore:

$$m*g*AB = F_C*AC\qquad [\text{equation 2}]$$

The torque $F_C*AC$ provides static balancing, such that properly chosen values of $F_C$ and AC results in a balance in which the sum of the torques in the system $\Sigma M_A(\phi)$ equals zero.

Figure 3:
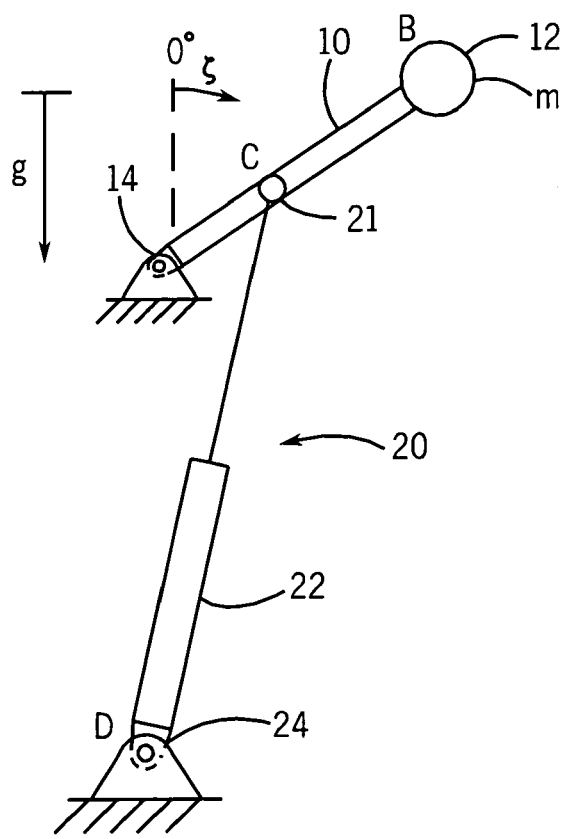
FIG. 3 is an illustration of a linear actuator mechanism working directly on the rotatable arm.

Referring now to FIG. 3, a balancing mechanism 20 for providing the opposing torque described above is shown. The mechanism 20 comprises a linear actuator 22 coupled between a pivotal or rotational axis 28 and a contact point 21 on the arm 10, the contact point 21 being provided between the axis of rotation of the arm 14 and the body 12 of mass "m" The statically unbalanced mass m, with center of gravity "B" is rotatable around the "A" axis 14, due to the force of gravity, as described above, to provide a torque "$M_A(\phi)$" which, when not in a static position, provides unbalance in the system. The unbalance is dependent on the angle of rotation $\phi$, and is directed to drive the mass "m" to the rotation angle of $\phi$-180°. As the center of mass "B" rotates on a circular path around the axis 14, the active contact point 21 of the linear actuator 20 also rotates on a circular path, at the same angle, thus the linear actuator 20 provides a nearly constant force in a direction opposite the torque of the arm and opposing the vector of gravity at the active contact point 21. The linear actuator 20 is coupled to a rotation axis 24 and is able to be rotated or pivoted around it.

Figure 4:
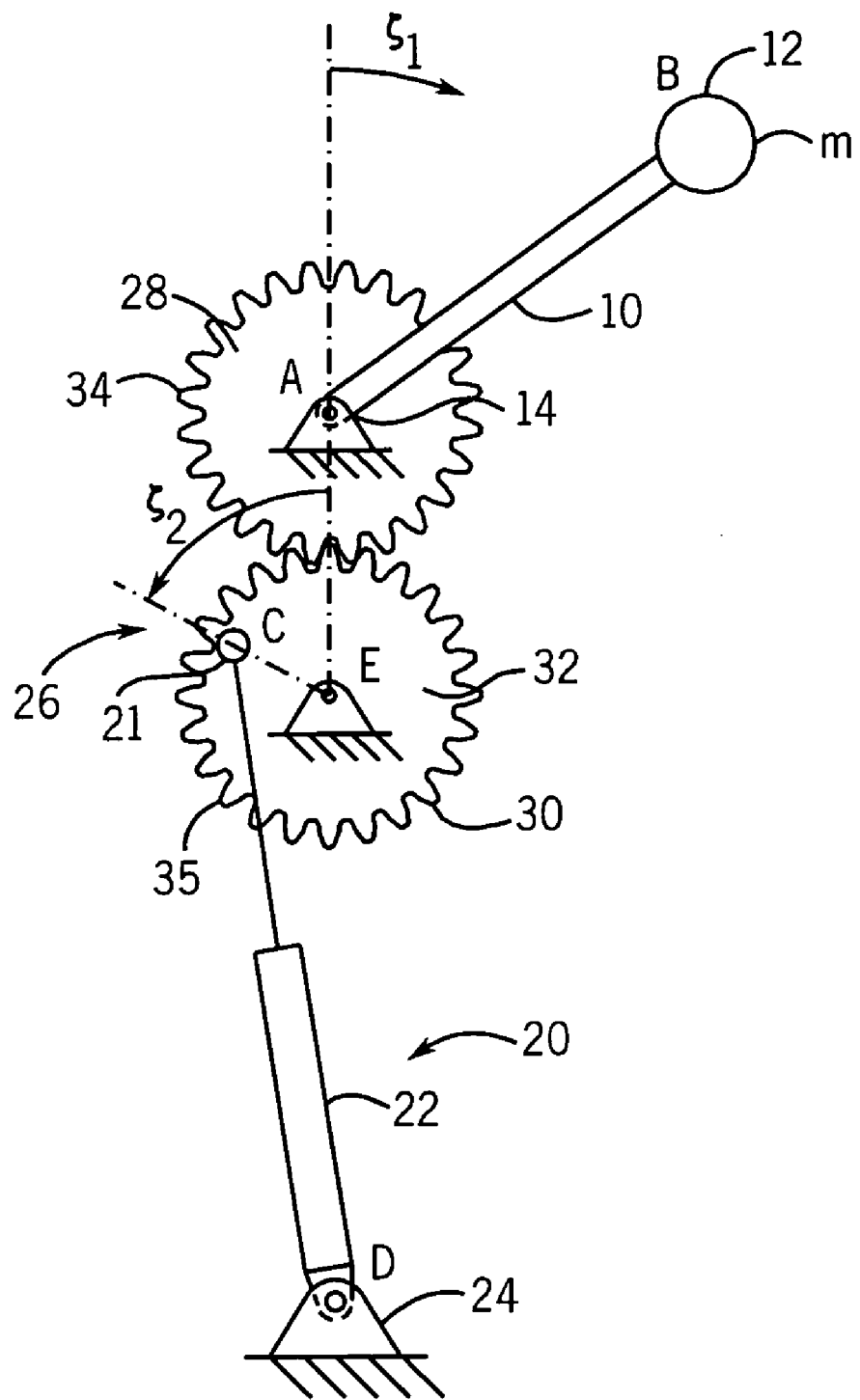
FIG. 4 is an illustration of a balancing mechanism including a linear actuator and a gear drive for applying a counteractive force to the rotatable arm.

Referring now to FIG. 4, a balancing mechanism 20 in which the balanced body 12 is separated from the linear actuator 22 by a gear drive 26 is shown. The gear drive 26 comprises a first cogwheel 28, a second cogwheel 30, and a linear actuator 22 extending from a pivot point 24 to an active contact point 21 on the cogwheel 30. The cogwheel 28 is fixed to the unbalanced body 12 of mass m and center of mass B and is rotatable about the same axis 14 as the arm 10. The active point of the balancing linear actuator 22 is connected to the contact point 21 of the cogwheel 30, which rotates about the axis 32. The cogwheels 28 and 30 are equivalent in size and each include a plurality of teeth 34 and 35, respectively, extending from the outer diameter of each of the cogwheels 28 and 30, and are assembled such that the angle of rotation $\phi_2$ of the linear actuator 22 is equal in magnitude to the angle of rotation $\phi_1$ of the arm 10, which results in a balancing machine with properties similar to those described above with reference to FIG. 3. As shown here, and in FIGS. 5, 6, and 8 below, the balancing mechanism is shown in a vertical configuration. The balancing mechanism, however, can be built in any direction, provided that when the linear actuator is at a maximum position, the arm is in upward position.

Figure 5:
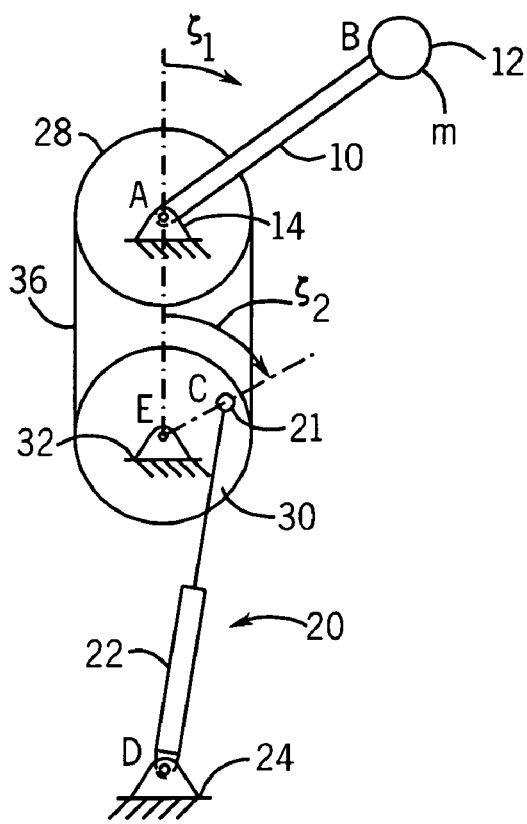
FIG. 5 is an illustration of an alternate embodiment of a balancing mechanism.

Referring now to FIG. 5, a second embodiment of the gear drive 26 is shown. Here, the cogwheels 28 and 30 are driven by a synchronous belt or chain 36, the belt or chain 36 providing a 1:1 ratio of motion between the wheels 28 and 30 such that an angular rotation of the cogwheel 28 results in an equal rotation of the cogwheel 30. The angle of rotation of the contact point 21 of the linear actuator 22 $\phi_2$ therefore equals the angle of rotation of the arm 10 ($\phi_1$).

Figure 6:
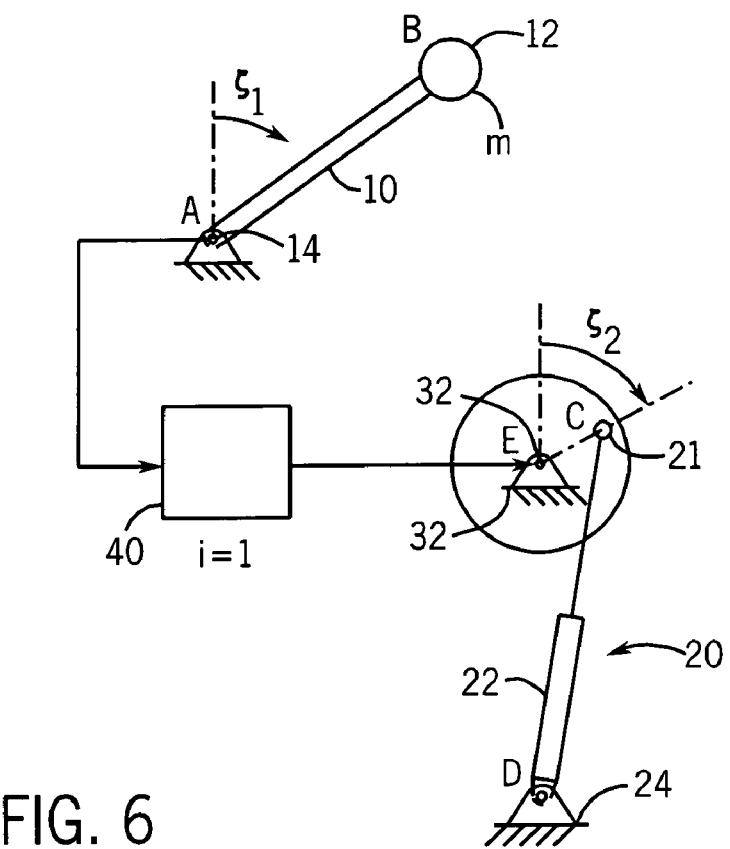
FIG. 6 is a block diagram of a balancing mechanism for balancing a rotatable arm.

Referring now to FIG. 6, a generalized drive mechanism 40 for synchronizing the motion of the linear actuator 22 and the arm 10 is shown. Here, the linear actuator 22 is coupled to a rotational member which can be, for example a wheel, a non-zero length arm or a cogwheel 30 as shown. The cogwheel 30 is coupled to a drive mechanism 40 which provides a synchronized connection between the rotational axes of the unbalanced mass 12 and the balancing mechanism 20. The "black box" drive mechanism 40 is selected to provide an angle of rotation of the cogwheel 30 that is equivalent to that of the arm 10 such that the angles of rotation of the arm 10 and of the contact point 21 of the linear actuator 12 are equivalent, and the counteractive force provided by the linear actuator 22 therefore counteracts that of the torque of the arm 10, balancing the system as described above.

Figure 7:
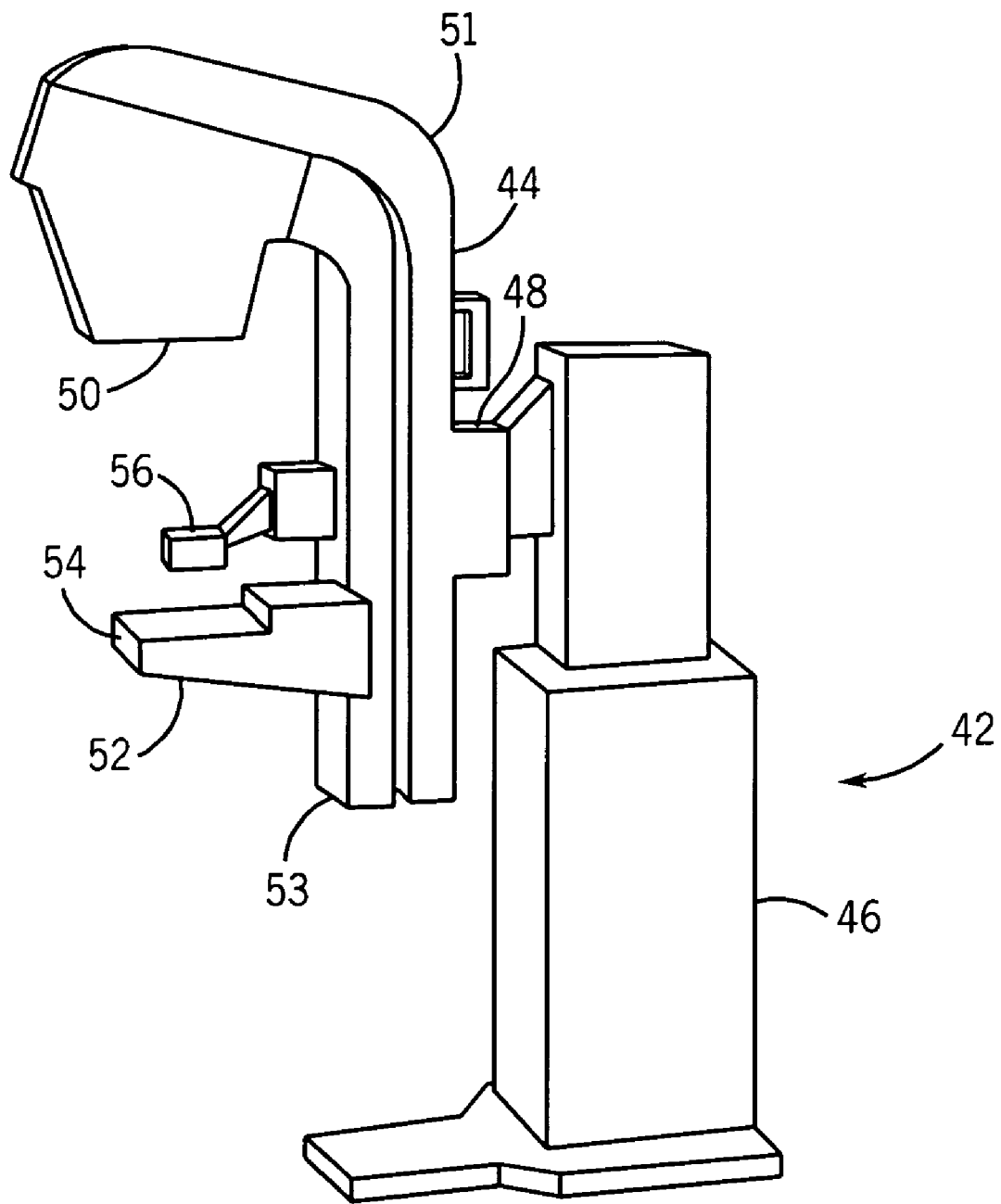
FIG. 7 is a perspective view of a typical mammography system.

Referring now to FIG. 7, an X-ray apparatus 42 rotatably mounted to an arm 44 is shown. Here, the X-ray apparatus 42 is a mammography system, comprising the arm 44 rotatably mounted to a base support 46 through a rotatable member 48. An X-ray source 50 is coupled to a first end 51 of the arm 44, and an X-ray detector 52 is coupled proximate an opposing end 53, the X-ray source 50 extending substantially perpendicular to the arm and directed toward the X-ray detector 52, which also extends from the arm such that the detector 52 receives radiation produced by the source 50. A breast support plate 54, and a breast compression plate 56, are positioned between the X-ray source 50 and the X-ray detector 52.

Figure 8:
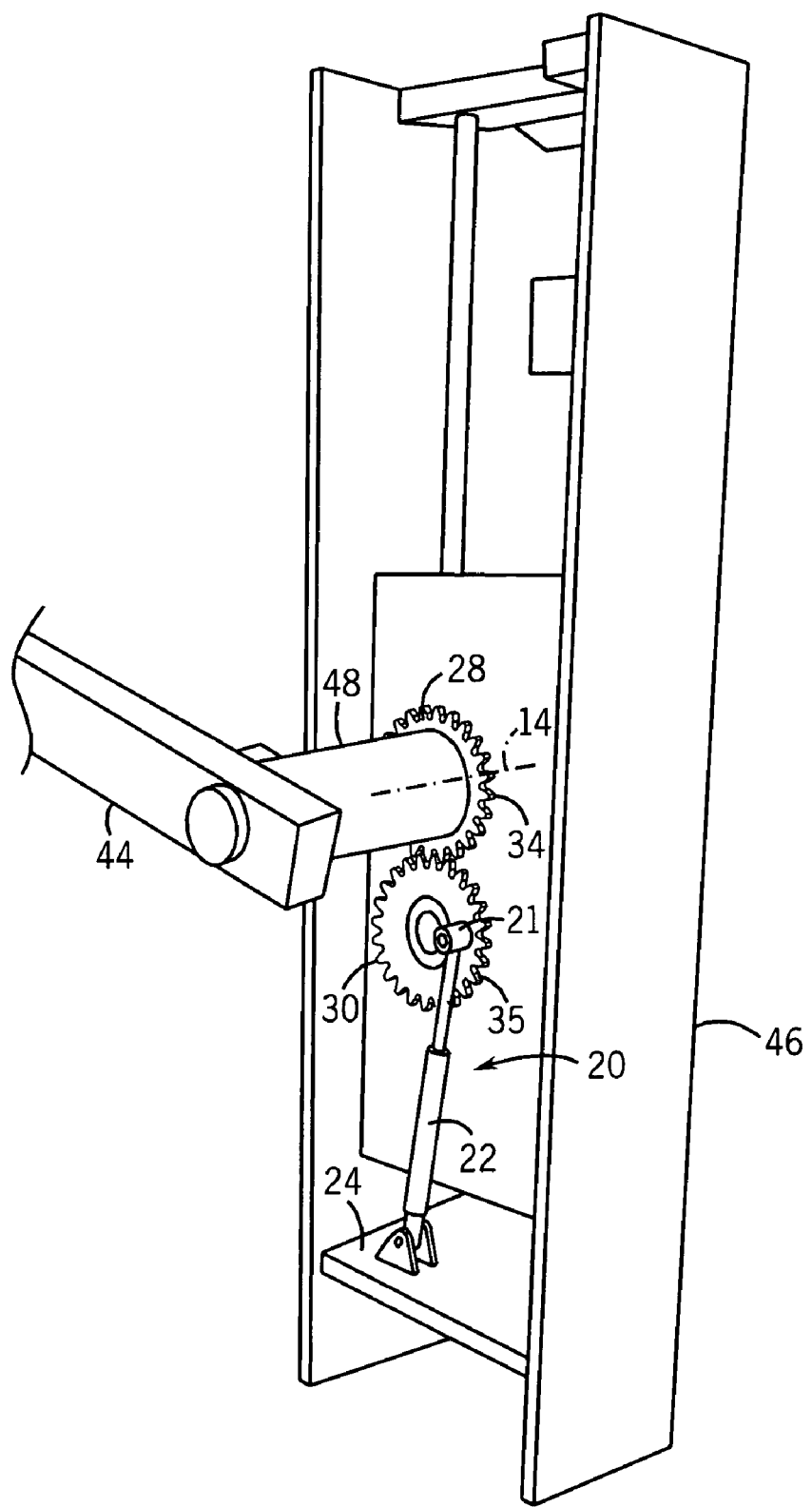
FIG. 8 is a perspective view of a support base for a mammography system incorporating a balancing mechanism as described herein with a housing removed to illustrate the balancing mechanism.

Referring now to FIG. 8, the base support 46 is shown with the front housing removed to provide a view of the balancing mechanism 20 including gear device 26. Here, the gear drive 26 comprises a first cogwheel 28 coupled to the rotating member 48 and disposed to rotate with the rotatable member 48 in the same axis of rotation 14 with the arm 44. A linear actuator 22 is coupled between a pivot point 24 provided in a wall of the base support 46, and an active contact point 21 on the second cogwheel 30 such that contact point 21 of the linear actuator 22 rotates with the second cogwheel 30. The linear actuator 22 applies the opposing force to the torque of the arm 10 to balance the system, and is therefore selected to provide a relatively constant force, as differentiations in the applied force can degrade the efficiency of the balancing. Suitable linear actuators include a spiral spring, gas spring, pneumatic power cylinder, hydraulic power cylinder, or similar devices which will be apparent to those of skill in the art.

The first and second cogwheels 28 and 30 are equivalent in size, and each include a plurality of teeth 34 and 35, respectively extending from the outer diameter of the wheel, such that the teeth 34 of the first cogwheel 28 mesh with the teeth 35 of the second cogwheel 30. Therefore, as the arm 44 is rotated, the first cogwheel 28 rotates, causing the second cogwheel 30 to rotate. The number of teeth 35 provided on the second cogwheel 30 is equivalent to the number of teeth 34 on the first cogwheel 28, wherein as the arm 44 is rotated, a 1:1 angular correspondence is maintained between the first and second cogwheels 28 and 30, respectively. Although the cogwheels 28 and 30 are shown as of the same size with an equivalent number of teeth, varying ways of gearing the drive system 26 provided by the cogwheels 28 and 30 will be apparent to those of ordinary skill in the art.

In operation, initial images are acquired with the arm 44 in the zero degree position. After images are acquired in this position, the clinician conducting the test typically rotates the arm 44 to a ninety degree position for additional image acquisition. As the arm is rotated, the first cogwheel 28 rotates, causing the second cogwheel 30 also to rotate. The contact point 21 of the linear actuator 20 is also rotated out of position, and applies a nearly constant upward force which, due to the intermeshed cogwheels 28 and 30, is maintained at an angle equivalent to the angle of rotation of the arm 44, such that the linear actuator 20 provides a counteractive force to the torque of the arm 44. The counteractive force is selected to balance the system such that the amount of force required to rotate the arm 44 is significantly reduced. Furthermore, the balancing mechanism eliminates the need for heavy counterweights, also reducing the overall weight of the X-ray system significantly.

Although the system has been described with reference to an X-ray source and detector, a balancing mechanism as described above can be used in any unbalanced system, including other types of imaging apparatuses, and particularly those in which a source and detector are provided on opposite ends of a rotatable arm. Other applications will be apparent to those of skill in the art.

While there has been shown and described what are at present considered the preferred embodiments of the invention, it will be obvious to those skilled in the art that various changes and modifications can be made therein without departing from the scope of the invention defined by the appended claims.

We claim:

1. An X-ray apparatus, comprising:
    a base support;
    an arm rotatably coupled to a first pivot point on the base support an X-ray source and an X-ray detector being coupled to opposing ends of the arm;
    a linear actuator, pivotally coupled to the base support at a first end and coupled to a contact point on a rotational member rotatably coupled to a second pivot point at a second end;
    a drive mechanism coupled between the rotational member and the arm, wherein as the arm is rotated the drive mechanism synchronizes the angle of rotation of the arm about the first pivot point with the angle of rotation of the linear actuator about the second pivot point such that a one to one correspondence is maintained between the angle of rotation of the arm and the angle of rotation of the linear actuator and a force applied by the linear actuator balances a torque of the arm.

2. The X-ray apparatus as defined in claim 1, wherein the linear actuator comprises a gas spring.

3. The X-ray apparatus as defined in claim 1, wherein the rotational member is a cogwheel driven in synchronous motion with the arm by the drive mechanism.

4. The X-ray apparatus as defined in claim 3, wherein the drive mechanism comprises a second cogwheel coupled to the pivot point of the arm to rotate with the arm, the second cogwheel being meshed with the cogwheel of the linear actuator to synchronize motion of the arm and the linear actuator.

5. The X-ray apparatus as defined in claim 4 wherein the cogwheel and the second cogwheel each include a plurality of teeth, the number of teeth on the cogwheel being equivalent to the number of teeth on the second cogwheel.

6. The X-ray apparatus as defined in claim 4, further comprising a belt, the belt being coupled to each of the cogwheels to synchronize rotation of the cogwheels.

7. The X-ray apparatus as defined in claim 1, wherein the drive mechanism comprises a rotational member coupling the arm to the base support.

8. An X-ray apparatus, comprising:
    a base support;
    a rotational member pivotably coupled to the base support;
    an arm having a first and a second end, an X-ray source being coupled to the first end and an X-ray detector coupled to the second end, the arm being mounted to the rotational member for rotation relative to the base support;
    a first cogwheel coupled to the rotational member;
    a second cogwheel meshed with the first cogwheel; and
    a constant force linear actuator, coupled to the second cogwheel at an active connection point and pivotally coupled to the base support at an inactive connection point;
    wherein as the arm is rotated the first and second cogwheels maintain a one to one correspondence between an angle of rotation of the arm and an angle of rotation of the active connection point of the linear actuator, the constant force linear actuator applying a torsional force to counterbalance the torque force of the arm.

9. The X-ray apparatus as defined in claim 8, wherein the constant force linear actuator comprises at least one of a gas spring, a pneumatic power cylinder, a hydraulic cylinder or a spiral spring.

10. The X-ray apparatus as defined in claim 8, wherein the active connection point coupling the linear actuator to the second cogwheel is offset from the axis of rotation 14 of the second cogwheel.

11. The X-ray apparatus as defined in claim 8, wherein the first cogwheel and second cogwheel are substantially equivalent in diameter.

12. The X-ray apparatus as defined in claim 8, wherein the first cogwheel includes a plurality of teeth extending outwardly from the outer diameter, and the second cogwheel includes an equivalent plurality of teeth extending outward from the diameter of the wheel, wherein the plurality of teeth extending from the first cogwheel meet with the plurality of teeth extending from the second cogwheel.

13. The X-ray apparatus as defined in claim 8, wherein the first cogwheel is meshed with the second cogwheel with a chain.

14. The X-ray apparatus as defined in claim 8, wherein a force applied by the linear actuator is selected to counteract the torque force generated by the arm.

15. A mammography system, comprising:
- a base support
- an arm rotatably coupled to the base support;
- a linear actuator rotatably coupled to the base support at a first end and to a first rotational member at a second end, the linear actuator applying a linear force at a connection point coupling the linear actuator and the first rotational member;
- second rotational member coupled to the arm and an outer circumference of the second rotational member being coupled to an outer circumference of the first rotation member, wherein as the arm is rotated, the first and second rotational members synchronizes the angle of rotation of the arm with the angle of rotation of the connection point such that the applied force of the linear actuator counteracts the torque force of the arm to statically balance the system.

16. The mammography system of claim 15, wherein the second rotational member comprises a cogwheel rotating about the axis of the arm the cogwheel being meshed with the rotational member.

17. The mammography system of claim 15, wherein the second rotational member is coupled to the first rotational member with a belt.

* * * * *